US012655463B2

(12) United States Patent  
Thompson

(10) Patent No.: US 12,655,463 B2  
(45) Date of Patent: Jun. 16, 2026

(54) COMPOSITIONS AND METHODS FOR NUCLEIC ACID QUALITY DETERMINATION

(71) Applicant: Personal Genome Diagnostics Inc., Baltimore, MD (US)

(72) Inventor: John F. Thompson, Warwick, RI (US)

(73) Assignee: Personal Genome Diagnostics Inc., Baltimore, MD (US)

( * ) Notice: Subject to any disclaimer, the term of this patent is extended or adjusted under 35 U.S.C. 154(b) by 767 days.

(21) Appl. No.: 17/914,815

(22) PCT Filed: Mar. 30, 2021

(86) PCT No.: PCT/US2021/024962  
§ 371 (c)(1),  
(2) Date: Sep. 27, 2022

(87) PCT Pub. No.: WO2021/202583  
PCT Pub. Date: Oct. 7, 2021

(65) Prior Publication Data  
US 2023/0138540 A1      May 4, 2023

Related U.S. Application Data

(60) Provisional application No. 63/002,785, filed on Mar. 31, 2020.

(51) Int. Cl.  
*C12Q 1/6806* (2018.01)  
*C12Q 1/6809* (2018.01)  
*C12Q 1/686* (2018.01)  
*C12Q 1/6876* (2018.01)

(52) U.S. Cl.  
CPC ......... *C12Q 1/6806* (2013.01); *C12Q 1/6809* (2013.01); *C12Q 1/686* (2013.01); *C12Q 1/6876* (2013.01); *C12Q 2600/16* (2013.01)

(58) Field of Classification Search  
CPC .... C12Q 1/6806; C12Q 1/6809; C12Q 1/686; C12Q 1/6876; C12Q 2600/16; C12Q 2525/151; C12Q 2525/204; C12Q 2549/119  
See application file for complete search history.

(56) References Cited

U.S. PATENT DOCUMENTS

| | | | |
|---|---|---|---|
| 2002/0025525 A1 | 2/2002 | Shuber | |
| 2007/0031847 A1* | 2/2007 | Cargill | C12Q 1/6883 536/23.2 |
| 2009/0311672 A1* | 12/2009 | Nunn | C12Q 1/6848 435/6.1 |
| 2013/0315886 A1 | 11/2013 | Gage et al. | |
| 2014/0051075 A1 | 2/2014 | Sinha | |

FOREIGN PATENT DOCUMENTS

| | | |
|---|---|---|
| CN | 104718300 A | 6/2015 |
| WO | 0222874 A2 | 3/2002 |
| WO | 2004058052 A2 | 7/2004 |
| WO | 2004081186 A2 | 9/2004 |
| WO | 2011097503 A2 | 8/2011 |
| WO | 2016109604 A2 | 7/2016 |
| WO | 2016109604 A3 | 9/2016 |
| WO | 2019219157 A1 | 11/2019 |

OTHER PUBLICATIONS

Buck et al., BioTechniques; 27:528-536 (Year: 1999).*  
Doucet et al., Methods Mol. Biol. 2016; 1400: 79-93, (Year: 2016).*  
Office Action issued in CN202180025679.8 dated May 30, 2025, 23 pages.  
Canadian Application No. 3176620, Office Action mailed on Dec. 12, 2023, 4 pages.  
European Application No. 21781247.8, Extended European Search Report mailed on Mar. 22, 2024, 9 pages.  
Ewing et al., "Human DNA Quantification and Sample Quality Assessment: Developmental Validation of the PowerQuant® System", Forensic Science International: Genetics, vol. 23, Apr. 16, 2016, pp. 166-177.  
United Kingdom Application No. 2214558.5, First Examination Report date of report Jul. 8, 2024, 3 pages.  
Internation Application No. PCT/US2021/024962, International Preliminary Report on Patentability mailed on Oct. 13, 2022, 14 pages.  
International Search Report and Written Opinion of PCT Application No. PCT/US2021/0124962 dated Oct. 5, 2021: pp. 1-20.  
Anonymous, "Mus musculus chromosome 5, clone RP23-41J13, complete sequence," Nov. 23, 2004, retrieved Sep. 3, 2021: pp. 1-2, <https://www.ncbi.nlm.nih.gov/nuccore/AC138265>.  
Anonymous, "Dicrocoelium dendriticum genome assembly D_dendriticum_Leon_v1_0_4, scaffold DDEL_scaffold0231954," Sep. 22, 2014, retrieved Sep. 3, 2021: p. 1, <https://www.ncbi.nlm.nih.gov/nuccore/LK649482>.  
Braasch et al., "Locked nucleic acid (LNA): fine-tuning the recognition of DNA and RNA," Chemistry & Biology, vol. 8(1), Jan. 2001: pp. 1-7.

* cited by examiner

*Primary Examiner* — Cynthia B Wilder  
(74) *Attorney, Agent, or Firm* — Kilpatrick Townsend & Stockton LLP

(57) ABSTRACT

Provided herein are compositions and methods for determining the quality of nucleic acids in a sample that includes a first set of primers and a second set of primers. Additionally, provided herein are compositions and methods for determining nucleic the acid quality in a sample including sets of primers for amplification of repetitive nucleic acid sequences.

42 Claims, 4 Drawing Sheets  
Specification includes a Sequence Listing.

1. HYBRID OLIGO WITH 3' END COMPLEMENTARY TO LINE ELEMENT WITH 3' END TM~50 ; 5' END NOT COMPLEMENTARY TO HUMAN DNA, TM~72

2. 3 - 5 CYCLES ELONGATION AT 50 FOR 2 MIN WITH HYBRID PRIMERS AND 5' END PRIMERS (ONLY HYBRID PRIMERS WILL EXTEND THOUGH INITIAL FEW CYCLES BECAUSE NO SUBSTRATE FOR 5' END PRIMERS)

3. 10 - 20 CYCLES ELONGATION AT 72 FOR 1 MIN ( ONLY 5' END PRIMERS WILL EXTEND)

4. SIZE ON TAPE STATION, LOOK AT LENGTH RATIOS

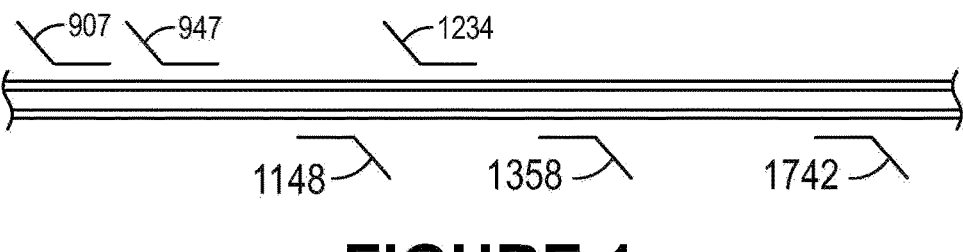

FIGURE 1

CHOICE OF LINE SEQUENCES FOR INITIAL PCR

| DF0000227 | | | | |
|---|---|---|---|---|
| RIGHT | LEFT | SEQUENCE | TM C | LENGTH |
| 909 | | GAGATATGTGACCTTTCAG (SEQ ID NO:3) | 52.3 | 19 |
| 954 | | AGGAAACTCAAAGAAATT (SEQ ID NO:4) | 50.7 | 18 |
| 1042 | | AGAATCAAGCAGAAATTC (SEQ ID NO:5) | 52.1 | 18 |
| | 1148 | CAGAAGAAAGAATTAGTGAG (SEQ ID NO:6) | 51.3 | 20 |
| 1234 | | TAGAAAATAGCCTCAAAAG (SEQ ID NO:8) | 52.0 | 19 |
| | 1358 | CCCAAACCTAGAGAAAG (SEQ ID NO:9) | 52.5 | 17 |
| | 1742 | AGAAATGCTAAAGGGAG (SEQ ID NO:11) | 52.2 | 17 |

| EXPECTED LENGTH (BP) | | | |
|---|---|---|---|
| | 1148 | 1358 | 1742 |
| 909 | 239 | 449 | 833 |
| 954 | 194 | 404 | 788 |
| 1041 | 104 | 317 | 701 |
| 1234 | - | 124 | 508 |

| NUMBER PREDICTED AMPLICONS | | | |
|---|---|---|---|
| | 1148 | 1358 | 1742 |
| 909 | 100 | 90 | 33 |
| 954 | 97 | 98 | 103 |
| 1042 | 113 | 92 | 97 |
| 1234 | - | 80 | 68 |

FIGURE 2

PRIMERS AND PRIMER COMPONENTS

| NAME | | 5' END COMMON SEQUENCE | TM C | NT |
|---|---|---|---|---|
| TOP/RIGHT | | TTCGGAACTCCTACGAGGTCCACT (SEQ ID NO:1) | 70 | 24 |
| BOTTOM/LEFT | | TCGCATCAGAGTCATCGTTGACC (SEQ ID NO:2) | 70.9 | 23 |
| DF0000227 | | | | |
| RIGHT | LEFT | 3' END SEQUENCE | TM C | LENGTH |
| 909 | | GAGATATGTGACCTTTCAG (SEQ ID NO:3) | 52.3 | 19 |
| 954 | | AGGAAACTCAAAGAAATT (SEQ ID NO:4) | 50.7 | 18 |
| 1042 | | AGAATCAAGCAGAAATTC (SEQ ID NO:5) | 52.1 | 18 |
| | 1148 | CTCACTAATTCTTTCTTCTG (SEQ ID NO:7) | 51.3 | 20 |
| 1234 | | TAGAAAATAGCCTCAAAAG (SEQ ID NO:8) | 52.0 | 19 |
| | 1358 | CTTTCTCTAGGTTTGGG (SEQ ID NO:10) | 52.5 | 17 |
| | 1742 | CTCCCTTTAGCATTTCT (SEQ ID NO:12) | 52.2 | 17 |

FIGURE 3

COMPOSITIONS AND METHODS FOR NUCLEIC ACID QUALITY DETERMINATION

CROSS-REFERENCE TO RELATED APPLICATIONS

This application claims the benefit under 35 USC § 119(e) to U.S. Application Ser. No. 63/002,785 filed Mar. 31, 2020. The disclosure of the prior application is considered part of and is incorporated by reference in the disclosure of this application.

INCORPORATION OF SEQUENCE LISTING

The material in the accompanying sequence listing is hereby incorporated by reference into this application. The accompanying sequence listing text file, name PGDX3150-1WO_SL.txt, was created on Mar. 15, 2021, and is 3,116 bytes. The file can be accessed using Microsoft Word on a computer that uses Windows OS.

BACKGROUND OF THE INVENTION

Field of the Invention

The invention relates generally to determination of the quality of nucleic acid in a sample and more specifically to determining the quality of nucleic acid before library preparation and sequencing.

Background Information

Determination of the quality of a nucleic acid sample such as DNA prior to extensive library preparation and sequencing is very useful so that time and money are not wasted on samples that are too degraded to be successfully analyzed. Current assays are based on DNA length or amplifiability. None of the assays is both sufficiently robust and predictive.

In principle, amplifiability is closest to the functional assessment of nucleic acid but it is done with a small number of specific fragments that do not always provide sufficient information. Thus, there exists a need for assays that are based on a broader range of nucleic acid sizes for analysis and that provide robust and predictive information.

SUMMARY OF THE INVENTION

The present invention relates to compositions and methods for determining nucleic acid quality using amplification of repetitive nucleic acid sequences.

In one embodiment, the invention provides a system for determining the quality of nucleic acid in a sample including: (a) a first set of primers including a plurality of first forward primers and a plurality of first reverse primers, each first forward primer and each first reverse primer including: (i) a 3' end sequence with complementarily to a repetitive sequence in the nucleic acid and having a first melting temperature; and (ii) a 5' end common sequence not present in the nucleic acid and having a second melting temperature, wherein the second melting temperature is greater than the first melting temperature; and (b) a second set of primers including a plurality of second forward primers and a plurality of second reverse primers, each second forward primer and each second reverse primer including a 5' end common sequence. In one aspect, the second melting temperature is greater than the first melting temperature by about 5° C. to 25° C. In one aspect, the first melting temperature is about 45° C. to 70° C. In one aspect, the second melting temperature is about 60° C. to 85° C. In one aspect, the first set of primers includes an equal number of first forward primers and first reverse primers. In one aspect, the first set of primers includes an unequal number of first forward primers and first reverse primers. In one aspect, the second set of primers includes an equal number of second forward primers and second reverse primers. In one aspect, the second set of primers includes an unequal number of second forward primers and second reverse primers. In one aspect, the first set of primers includes about 1 to 20 first forward primers and about 1 to 20 first reverse primers. In one aspect, the second set of primers includes about 1 to 20 second forward primers and about 1 to 20 second reverse primers. In one aspect, the repetitive nucleic acid sequence includes a retrotransposon. In one aspect, the retrotransposon is a L1 retrotransposon. In one aspect, the 5' end common sequence of each first forward primer includes a sequence of SEQ ID NO:1. In one aspect, the 5' end common sequence of each first reverse primer includes a sequence of SEQ ID NO:2. In one aspect, the 3' end sequence of each first forward primer includes a sequence of SEQ ID NO:3, SEQ ID NO:4, SEQ ID NO:5, SEQ ID NO:8, or any combination thereof. In one aspect, the 3' end sequence of each first reverse primer includes a sequence of SEQ ID NO:7, SEQ ID NO:10, SEQ ID NO:12, or any combination thereof.

In another embodiment, the invention provides a method for determining quality of nucleic acid in a sample including: a) preparing a polymerase chain reaction (PCR) mixture including: (i) a first set of primers including a plurality of first forward primers and a plurality of first reverse primers, each first forward primer and each first reverse primer including: (i) a 3' end sequence with complementarity to a repetitive sequence in the nucleic acid and having a first melting temperature; and (ii) a 5' end common sequence not present in the nucleic acid and having a second melting temperature, wherein the second melting temperature is greater than the first melting temperature; and ii) a second set of primers including a plurality of second forward primers and a plurality of second reverse primers, each second forward primer and each second reverse primer including a 5' end common sequence; (a) performing a first polymerase chain reaction (PCR) on the sample, wherein a first elongation step of each cycle in the first PCR is at a temperature of about the first melting temperature; (b) performing a second polymerase chain reaction (PCR) on the sample, wherein a second elongation step of each cycle in the second PCR is at a temperature of about the second melting temperature; and (c) determining a size range of amplicons. In one aspect, the second melting temperature is greater than the first melting temperature by about 5° C. to 25° C. In one aspect, the first melting temperature is about 45° C. to 70° C. In one aspect, the first elongation step is for about 2 minutes. In one aspect, the second elongation step is for about 1 minute. In one aspect, the first set of primers includes an equal number of first forward primers and first reverse primers. In one aspect, the first set of primers includes about 1 to 20 first forward primers and about 1 to 20 first reverse primers. In one aspect, the second set of primers includes about 1 to 20 second forward primers and about 1 to 20 second reverse primers. In one aspect, the repetitive nucleic acid sequence includes a retrotransposon. In one aspect, the retrotransposon is a L1 retrotransposon. In one aspect, the second PCR includes about 10 to 35 cycles.

In yet another aspect, the method further includes determining intensity ratios of amplicons. In one aspect, a presence of predicted amplicon sizes correlates with nucleic acid quality. In one aspect, the 5' end common sequence of each first forward primer includes a sequence of SEQ ID NO:1. In one aspect, the 5' end common sequence of each first reverse primer includes a sequence of SEQ ID NO:2. In one aspect, the 3' end sequence of each first forward primer includes a sequence of SEQ ID NO:3, SEQ ID NO:4, SEQ ID NO:5, SEQ ID NO:8, or any combination thereof. In one aspect, the 3' end sequence of each first reverse primer includes a sequence of SEQ ID NO:7, SEQ ID NO:10, SEQ ID NO:12, or any combination thereof.

BRIEF DESCRIPTION OF THE DRAWINGS

FIG. 1 shows an overview of primers and methods for polymerase chain reaction (PCR).

FIG. 2 shows representative LINE sequences for PCR for determining nucleic acid quality.

FIG. 3 shows representative primers and primer components for determining nucleic acid quality.

DETAILED DESCRIPTION OF THE INVENTION

Figure 4:
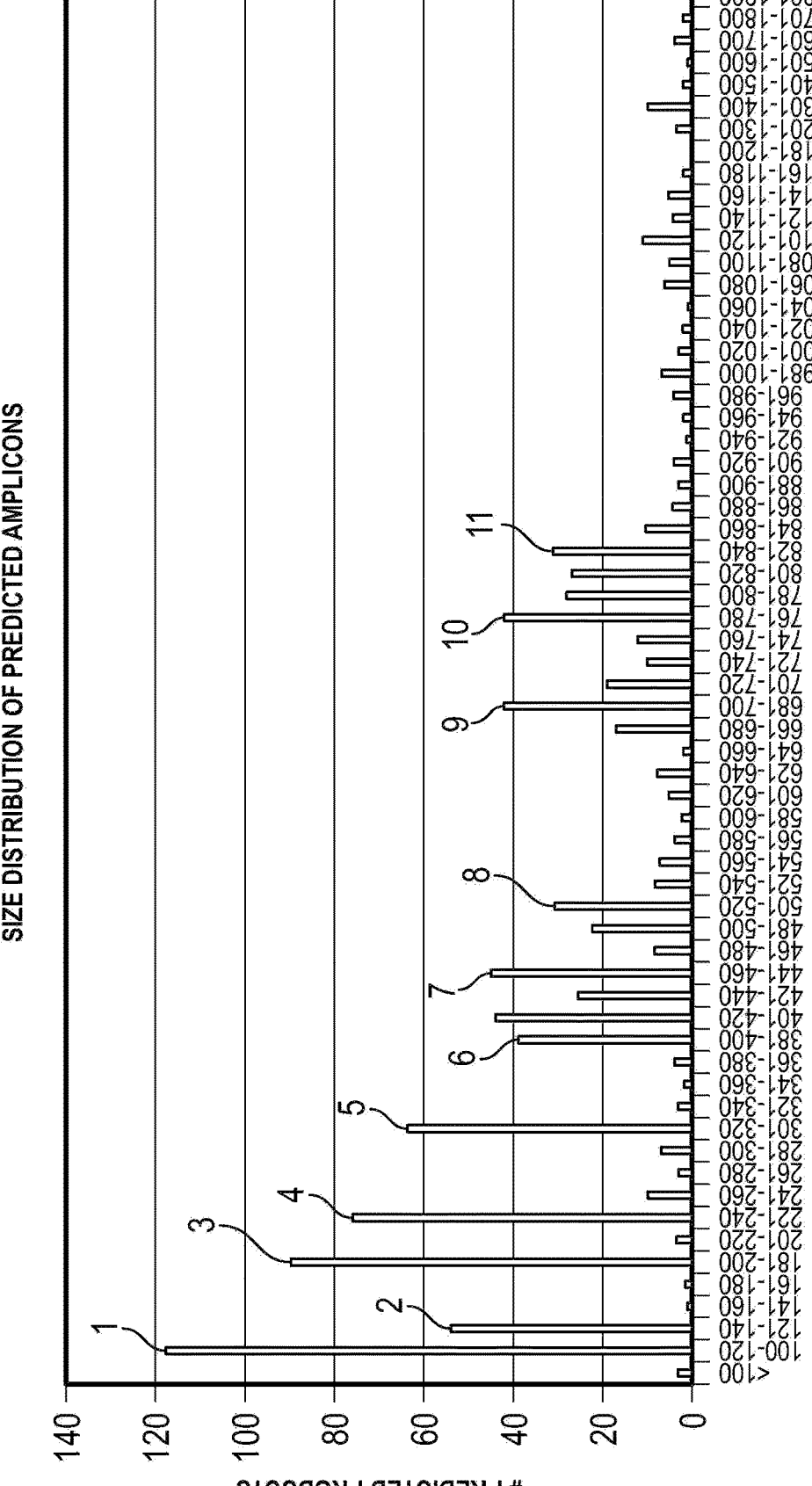
FIG. 4 shows a size distribution of predicted amplicons.

The present invention is based on the finding that amplification of repetitive sequences in the human genome using a small number of primers that can amplify hundreds or more distinct sites in the genome provides robust and accurate information on DNA quality. Such information is useful for library preparation and next generation sequencing (NGS), for example.

Provided herein are systems of oligonucleotide primers for determining quality of nucleic acid. Systems of oligonucleotide primers for determining nucleic acid quality provided herein can include a first set of oligonucleotide primers. Systems of oligonucleotide primers for determining nucleic acid quality provided herein can also include a second set of oligonucleotide primers.

The quality of any nucleic acid can be determined using the systems of oligonucleotide primers provided herein. The nucleic acid can be from any sample or from any type of sample. For example, the sample can be blood, saliva, plasma, serum, urine, or other biological fluid. Additional exemplary biological fluids include serosal fluid, lymph, cerebrospinal fluid, mucosal secretion, vaginal fluid, ascites fluid, pleural fluid, pericardial fluid, peritoneal fluid, and abdominal fluid. In some aspects, the sample is a tissue sample. In some aspects, the sample is a cell sample or single cells. Fresh samples or stored samples can be used, including, for example, stored frozen samples, formalin-fixed paraffin-embedded (FFPE) samples, and samples preserved by any other method.

The sample can be from a normal healthy subject. The sample can also be from a subject with a disease or disorder. The quality of nucleic acids in a sample from a subject with any disease or disorder can be determined using the systems of primers provided herein. In some aspects, the disease or disorder is cancer. In some aspects, the sample is a fluid sample from a subject with cancer. In some aspects, the sample is a tissue sample or a cell sample from a healthy subject or a subject with or suspected of having cancer. A cancer sample can be a sample from a solid tumor or a liquid tumor. The cancer can be kidney cancer, renal cancer, urinary bladder cancer, prostate cancer, uterine cancer, breast cancer, cervical cancer, ovarian cancer, lung cancer, colon cancer, rectal cancer, oral cavity cancer, pharynx cancer, pancreatic cancer, thyroid cancer, melanoma, skin cancer, head and neck cancer, brain cancer, hematopoietic cancer, leukemia, lymphoma, bone cancer, muscle cancer, sarcoma, rhabdomyosarcoma, and others. The disease or disorder can be infectious disease, for example, a viral, bacterial, fungal, or parasitic infection.

The quality of nucleic acids can be determined in a sample using invention primer systems for determining nucleic acid quality provided herein. Nucleic acids can also be extracted, isolated, or purified from a sample prior to determining nucleic acid quality. Any suitable method for extraction, isolation, or purification can be used. Exemplary methods include phenol-chloroform extraction, guanidinium-thio-cyanate-phenol-chloroform extraction, gel purification, and use of columns and beads. Commercial kits can be used for extraction, isolation, or purification of nucleic acids.

The quality of nucleic acids from any organism or species can be determined using the systems of primers provided herein. For example, the quality of nucleic acids from any animal, plant, or microorganism can be determined using the systems of primers provided herein. The quality of nucleic acids from any mammal can be determined, including nucleic acids from humans, rodents (including mice, rats, hamsters and guinea pigs), cats, dogs, rabbits, farm animals including cows, horses, goats, sheep, pigs, etc., and primates (including monkeys, chimpanzees, orangutans and gorillas), and others. The quality of nucleic acids from any other animal can be determined using the systems of primers provided herein, including nucleic acids from reptiles, birds, amphibians, bony fish, cartilaginous fish, and invertebrate animals, for example. The quality of nucleic acids from any angiosperm, any gymnosperm, any fern and related organisms, any hornwort, any liverwort, any moss, and any green algae, for example, can be determined. Exemplary microorganisms include any eukaryotic or prokaryotic unicellular organism, such as bacteria, archae, protists, protozoa, and fungi, and, viruses and viroids.

The quality of any type of nucleic acid can be determined using the system of primers provided herein, including DNA, RNA, and nucleic acid fragments, for example. DNA sources include, for example, chromosomal DNA, plasmid DNA, cDNA, cell-free DNA (cfDNA), circulating tumor DNA (ctDNA), and any fragment thereof. Reverse transcription can be performed on RNA by any suitable method to prepare DNA, with DNA quality determined using the systems of primers provided herein, After determining nucleic acid quality, nucleic acids can be used for the preparation of nucleic acid libraries, for example. In some aspects, the library is a genomic library. Nucleic acid libraries can be prepared by attaching sets or subsets of oligonucleotides that can include one or more barcodes for identification to nucleic acid molecules through end-repair, A-tailing, and adapter ligation, for example. Nucleic acids and libraries of nucleic acids can be analyzed by next generation sequencing (NGS), for example. Any suitable sequencing method can be used to analyze nucleic acids. Exemplary NGS methodologies include the Roche 454 sequencer, Life Technologies SOLiD systems, the Life Technologies Ion Torrent, BGI/MGI systems, Genapsys systems, and Illumina systems such as the Illumina Genome Analyzer II, Illumina MiSeq, Illumina HiSeq, Illumina NextSeq, and Illumina NovaSeq instruments.

Systems of oligonucleotide primers provided herein can include a first set of primers. A first set of primers can include a plurality of first forward primers. A first set of primers can also include a plurality of first reverse primers. As used herein, the terms "forward primer" and "reverse primer" can be used interchangeably with the terms "+ strand primer" and "– strand primer," respectively, unless context clearly indicates otherwise. Each first forward primer and each first reverse primer of a plurality of first forward primers and a plurality of first reverse primers can include a 3' end sequence with complementarity to a repetitive sequence in the nucleic acid whose quality is determined using the systems of primers provided herein. Each first forward primer and each first reverse primer of a plurality of first forward primers and a plurality of first reverse primers can also include a 5' end common sequence not present in the nucleic acid whose quality is determined. Accordingly, primers included in a first set of primers can be hybrid primers. As used herein, the term "hybrid primer" means a primer having at least two sequences with complementarity to at least two sequences in a nucleic acid molecule that are not contiguous or not adjacent to each other in the nucleic acid molecule or with at least one of the at least two sequences initially not present in the nucleic acid molecule. As an example, where a hybrid primer includes a 3' end sequence complementary to a nucleic acid sequence and a 5' end sequence without complementarity to the nucleic acid, nucleic acid molecules with sequences complementary to the 5' end sequence of a hybrid primer can be generated by polymerase chain reaction (PCR), for example, thereby generating nucleic acid molecules with complementarity to both the 3' end and 5' end sequences of the hybrid primer.

As used herein the terms "complementary" and "complementarity" refer to the ability of polynucleotides to form base pairs with one another. Base pairs are typically formed by hydrogen bonds between nucleotides in anti-parallel polynucleotide strands. Complementary polynucleotide strands can base pair in the Watson-Crick manner (e.g., A to T, A to U, C to G), or in any other manner that allows for the formation of duplexes. As persons skilled in the art appreciate, when using RNA as opposed to DNA, uracil rather than thymine is the base that is considered to be complementary to adenosine.

Perfect or complete complementarily or 100% complementarily refers to a situation in which each nucleotide of one polynucleotide strand can hydrogen bond with a nucleotide of an anti-parallel polynucleotide strand. Less than perfect complementarily refers to a situation in which some, but not all, nucleotides of two strands can hydrogen bond with each other. For example, for two 20-mess, if only two base pairs on each strand can hydrogen bond with each other, the polynucleotide strands exhibit 10% complementarity. As another example, if 18 nucleotides out of 20 nucleotides on each strand can hydrogen bond with each other, the polynucleotide strands exhibit 90% complementarity, "Substantial complementarity" refers to polynucleotide strands exhibiting 75% or greater complementarity, excluding regions of the polynucleotide strands, such as overhangs, that are selected to be non-complementary. Accordingly, complementarity does not consider overhangs that are selected to not be similar or complementary to the nucleotides on the anti-parallel strand, unless context clearly indicates otherwise. In some aspects, 3' end sequences with complementarity to repetitive nucleic acid sequences exhibit perfect or complete complementarity to repetitive nucleic acid sequences. In some aspects, 3' end sequences with complementarity to repetitive nucleic acid sequences exhibit substantial complementarity to repetitive nucleic acid sequences.

As used herein, "5' end common sequence" means that some or all forward primers include the same sequence or substantially the same sequence at the 5' end of the primer and some or all reverse primers include the same sequence or substantially the same sequence at the 5' end of the primer. For example, a 5' end common sequence of first forward primers and second forward primers (described below) can include the same sequence and can also include additional nucleotides 5', 3' or both 5' and 3' of the 5' end common sequence. As another example, a 5' end common sequence of first reverse primers and second reverse primers (described below) can include the same sequence and can also include additional nucleotides 5', 3' or both 5' and 3' of the 5' end common sequence. 5' end common sequences of forward primers can be the same or different. For example, forward primers can include more than one 5' end common sequence that is shared among forward primers, such as two, three, four, five, six, seven, eight, nine, ten, or more different 5' end common sequences. 5' end common sequences of reverse primers can be the same or different. For example, reverse primers can include more than one 5' end common sequence that is shared among reverse primers, such as two, three, four, five, six, seven, eight, nine, ten, or more different 5' end common sequences. 5' end common sequences of forward primers and reverse primers can the same or different. Any sequence not present in a nucleic acid that is amplified can be a 5' end common sequence.

As used herein, "3' end sequence" when referring to primer sequences means a sequence at the 3' end of each first forward primer and each first reverse primer that can vary. 3' end sequences of first forward primers and first reverse primers can be of any length, including about 15, about 16, about 17, about 18, about 19, about 20, about 21, about 22, about 23, about 24, about 25, about 26, about 27, about 28, about 29, about 30, about 31, about 32, about 34, about 35 nucleotides. Any number of different 3' end sequences can be included in first forward primers and first reverse primers of a first set of primers provided herein. For example, first forward primers and first reverse can include about 1, about 2, about 3, about 4, about 5, about 6, about 7, about 8, about 9, about 10, about 11, about 12, about 13, about 14, about 15, about 16, about 17, about 18, about 19, about 20 different 3' end sequences.

Any combination of different numbers of 3' sequences can be included in first forward primers and first reverse primers. For example, first forward primers can have four different 3' end sequences. First forward primers can include a sequence of SEQ ID NO:3, SEQ ID NO:4, SEQ ID NO:5, SEQ ID NO:8, or any combination thereof. In some aspects, first reverse primers include three different 3' end sequences. In some aspects, first reverse primers include a sequence of SEQ ID NO:7, SEQ ID NO:10, SEQ ID NO:12, or any combination thereof. Accordingly, first sets of primers of the systems of primers provided herein can include an unequal number of first forward primers and first reverse primers. As an example, first forward primers can include four different 3' end sequences and a 5' end common sequence, and first reverse primers can include three different 3' end sequences and a 5' end common sequence. A first set of primers of the systems of primers provided herein can also include an equal number of first forward primers and first reverse primers. As an example, first forward primers and first reverse primers can include the same number of different 3' end sequences and a 5' end common sequence. In some aspects, the first set of primers includes about 1 to 20 first forward primers. In some aspects, the first set of primers includes about 1 to 20 first reverse primers. A first set of primers can include any number of first forward primers and any number of first reverse primers.

5' end common sequences can be of any length, including about 15, about 16, about 17, about 18, about 19, about 20, about 21, about 22, about 23, about 24, about 25, about 26, about 27, about 28, about 29, about 30, about 31, about 32, about 34, about 35 nucleotides. 5' end common sequences of first forward and first reverse primers can include the same or substantially the same sequences. 5' end common sequences of first forward primers and first reverse primers can include any sequence that is not present in the nucleic acid analyzed for quality using the primer systems provided herein. In some aspects, 5' end common sequences of first forward primers include a sequence of SEQ ID NO:1. In some aspects, 5' end common sequences of first reverse primers include a sequence of SEQ ID NO:2.

3' end sequences of first forward and first reverse primers included in primer systems for determining nucleic acid quality provided herein can have a first melting temperature. 5' end common sequences of first forward and first reverse primers included in primer systems for determining nucleic acid quality provided herein can have a second melting temperature. The second melting temperature can be greater than the first melting temperature. In some aspects, the second melting temperature is greater than the first melting temperature by about 5° C. to 25° C. The first melting temperature can be about 45° C. to 70° C. The first melting temperature can be about 45° C. to 50° C., about 45° C. to 55° C., about 45° C. to 60° C., about 45° C. to 65° C., about 45° C. to 70° C., In some aspects, by way of example, the first melting temperature is about 70° C. to 65° C., about 70° C. to 60° C., about 70° C. to 55° C., about 70° C. to 50° C., about 70° C. to 45° C. In some aspects, the first melting temperature is about 50° C. to 53° C. In some aspects, the first melting temperature is about 50.7° C. to 52.5° C. Generally, melting temperatures of 3' end sequences of first forward and first reverse primers are within 0.1° C., 0.5° C., 1.0° C., 1.5° C., 2.0° C., 2.5° C., 3.0° C., 3.5° C., 4.0° C., 4.5° C., 5.0° C., and any number or range in between, of each other.

The second melting temperature can be about 60° C. to 85° C. In some aspects, by way of example, the second melting temperature is about 60° C. to 85° C., about 60° C. to 80° C., about 60° C. to 75° C., about 60° C. to 70° C., about 60° C. to 65° C. In some aspects, the second melting temperature is about 80° C. to 85° C., about 75° C. to 85° C., about 70° C. to 85° C., about 65° C. to 85° C., about 60° C. to 85° C. In some aspects, the second melting temperature is about 70° C. to 75° C. In some aspects, the second melting temperature is about 70° C. to 73° C. In some aspects, the second melting temperature is about 70° C. to 72° C. In some aspects, the second melting temperature is about 70° C. to 71° C. In some aspects, the second melting temperature is about 70° C. to 70.9° C.

First forward primers and first reverse primers of first primer sets provided herein can include a 3' end sequence with complementarity to a repetitive sequence in the nucleic acid whose quality is determined using the systems of primers provided herein. The repetitive nucleic acid sequence can include a retrotransposon. Retrotransposons, also called Class I transposable elements or transposons via RNA intermediates, are genetic elements that can copy and paste themselves into different genomic locations by converting RNA into DNA through reverse transcription via an RNA transposition intermediate.

Types of retrotransposons include LTR and non-LTR retrotransposons. LTR retrotransposons are over 5 kilobases in size. LTR retrotransposons include long strands of repetitive DNA at each end of the retrotransposon that are termed long terminal repeats (LTRs). Exemplary LTR retrotransposons include Ty1-copia-like (Pseudoviridae), Ty3-gypsy-like (Metaviridae), and BEL-Pao-like groups of retrotransposons. Millions of copies per haploid nucleus of Ty1-copia-like and Ty3-gypsy-like groups of retrotransposons can be found in animal, fungal, protist, and plant genomes, while BEL-Pao like elements can only be found in animals.

Non-LTR retrotransposons include long interspersed nuclear elements (LINEs) and short interspersed nuclear elements (SINEs). LINE transcripts include an RNA polymerase II promoter that allows the LINE to be copied after insertion into a site of the genome. The LINE transcript is the transposition intermediate that moves from the nucleus to the cytoplasm for translation of reverse transcriptase. Reverse transcriptase generates a DNA copy of the LINE RNA that can integrate into a new site of the genome. Each LINE is about 7,000 basepairs (bp) long, with an estimated 100,000 truncated to 4,000 full-length LINE-1 elements present in the human genome. Many LINEs are not transcribed or translated because of accumulation of mutations. Five main groups of LINES include the L1, RTE, R2, I, and Jockey groups. Human LINEs include LINE-1/L1 and remnants of L2 and L3. The human genome includes about 850,000 LINE elements, with about 516,000 copies of L1 elements, about 315,000 copies of L2 elements, and about 37,000 copies of L3 elements. The LINE-1/L1 element is widely found in mammals and still active in the human genome. Additional LINE elements include Tad, CRE, Deceiver, and Inkcap-like elements.

SINE elements include non-autonomous, non-coding transposable elements (TEs) of about 100 to 700 bp. Three types of SINE elements include CORE-SINEs, V-SINEs, and AmnSINEs. SINE elements are transcribed by RNA polymerase III, with transcribed regions including promoter elements. SINE elements do not encode proteins and likely use proteins coded by LINES for reverse transcription and integration into the genome. Exemplary SINES include Alu elements that are short-interspersed nuclear elements of about 300 nucleotides and that can be found in humans and other species. Alu elements are the most common SINE in humans, with more than 1,000,000 copies throughout the human genome. Additional exemplary SINEs include SINE_Cf repeats of canines, and Au-SINEs and Angio-SINEs of plants.

3' end sequences of first forward primers and first reverse primers of first primer sets can have complementarity to a sequence of any retrotransposon from any organism. For example, 3' end sequences of first forward and first reverse primers can be designed based on the source of nucleic acid whose quality is determined using the systems of primers provided herein. Thus, 3' end sequences can have complementarity to retrotransposons found in the organism the nucleic acid whose quality is determined is obtained from. The nucleic acid can be from a human. In some aspects, the retrotransposon is a L1 retrotransposon.

3' end sequences of first forward and first reverse primers can be designed to have complementarity to staggered sequences along both strands of a retrotransposon. Staggered sequences along both strands of a retrotransposon can be non-overlapping. In some aspects, each first forward primer generates amplicons with each first reverse primer, and each first reverse primer generates amplicons with each first forward primer. In this manner, numerous amplicons can be generated along a range of sizes, including about 50 to 200 bp, about 50 to 300 bp, about 50 to 400 bp, about 50 to 500 bp, about 50 to 600 bp, about 50 to 700 bp, about 50 to 800 bp, about 50 to 900 bp, about 50 to 1,000 bp, about 50 to 1,500 bp, about 50 to 2,000 bp, about 50 to 2,500 bp, about 50 to 3,000 bp, about 50 to 3,500 bp, about 50 to 4,000 bp, about 50 to 4,500 bp, about 50 to 5,000 bp. In some aspects, amplicons range from about 100 to 2,000 bp.

System of primers for determining quality of nucleic acid in a sample can include a second set of primers. The second set of primers can include a plurality of second forward primers and a plurality of second reverse primers. Each second forward primer and each second reverse primer can include a 5' end common sequence.

A 5' end common sequence included in first forward and first reverse primers can be included in second forward and second reverse primers. For example, each forward primer can include the same sequence or substantially the same sequence at the 5' end of the primer and each reverse primer can include the same sequence or substantially the same sequence at the 5' end of the primer. As another example, a 5' end common sequence of first forward primers and second forward primers can include the same sequence and can also include additional nucleotides 5', 3' or both 5' and 3' of the 5' end common sequence. As another example, a 5' end common sequence of first reverse primers and second reverse primers can include the same sequence and can also include additional nucleotides 5', 3' or both 5' and 3' of the 5' end common sequence. 5' end common sequences of forward primers can be the same or different. 5' end common sequences of reverse primers can be the same or different. 5' end common sequences of forward primers and reverse primers can the same or different.

In some aspects, second forward and second reverse primers include only a 5' end common sequence included in first forward and first reverse primers and no other sequences or nucleotides. In some aspects, second forward and second reverse primers can include other sequences or nucleotides in addition to a 5' end common sequence included in first forward and first reverse primers. For example, second forward and second reverse primers can include 1, 2, 3, 4, 5, 6, 7, 8, 9, 10, or more additional nucleotides upstream or 5' of the 5' end common sequence. As another example, second forward and second reverse primers can also include 1, 2, 3, 4, 5, 6, 7, 8, 9, 10, or more additional nucleotides downstream or 3' of the 5' end common sequence. Additional nucleotides downstream or 3' of the 5' end common sequence can include 5' nucleotides present in the 3' end sequence of first forward and first reverse primers without including all of the nucleotides present in the 3' end sequence of first forward and first reverse primers. Thus, additional nucleotides included downstream or 3' of the 5' end common sequence of second forward and second reverse primers can extend into 3' end sequences included in first forward and first reverse primers. In some aspects, 3' end sequences included in second forward and second reverse primers include at least 5, at least 6, at least 7, at least 8, at least 9, at least 10, at least 11, at least 12, at least 13, at least 14, at least 15, at least 16, at least 17, at least 18, at least 19, at least 20 fewer 3' nucleotides than 3' end sequences included in first forward and first reverse primers. Accordingly, 3' end sequences of first forward and first reverse primers can include at least 5, at least 6, at least 7, at least 8, at least 9, at least 10, at least 11, at least 12, at least 13, at least 14, at least 15, at least 16, at least 17, at least 18, at least 19, at least 20 more 3' nucleotides than 3' end sequences included in second forward and second reverse primers.

Any combination of second forward and second reverse primers can be included in the second set of primers, including second forward primers that include a 5' end common sequence, second forward primers that include a 5' end common sequence and any number of additional nucleotides, second reverse primers that include a 5' end common sequence, and second reverse primers that include a 5' end common sequence and any number of additional nucleotides. Accordingly, the second set of primers can include an equal number of second forward and second reverse primers. A second set of primers can also include an unequal number of second forward and second reverse primers. In some aspects, the second set of primers includes about 1 to 20 second forward primers. In some aspects, the second set of primers includes about 1 to 20 second reverse primers. A second set of primers can include any number of second forward primers and any number of second reverse primers.

Second forward and second reverse primers can have a melting temperature that is greater than the first melting temperature of 3' end sequences of first forward and first reverse primers. The melting temperature of second forward and second reverse primers can be similar to or correspond to the second melting temperature of 5' end common sequences of first forward and first reverse primers. For example, where second forward and second reverse primers do not include sequences or nucleotides in addition to 5' end common sequences, the melting temperature of second forward and second reverse primers can correspond to the second melting temperature of 5' end common sequences included in first forward and first reverse primers. As another example, where second forward and second reverse primers include sequences or nucleotides in addition to 5' end common sequences, the melting temperature of second forward and second reverse primers can be greater than the second melting temperature of 5' end common sequences included in first forward and first reverse primers. The melting temperature of second forward and second reverse primers can be greater by about 0.5° C., 1.0° C., 1.5° C., 2.0° C., 2.5° C., 3.0° C., 3.5° C., 4.0° C., 4.5° C., 5.0° C., 5.5° C., 6.0° C., 6.5° C., 7.0° C., 7.5° C., 8.0° C., 8.5° C., 9.0° C., 9.5° C., 10.0° C., 10.5° C., 11.0° C., 11.5° C., 12.0° C., 12.5° C., 13.0° C., 13.5° C., 14.0° C., 14.5° C., 15.0° C., 15.5° C., 16.0° C., 16.5° C., 17.0° C., 17.5° C., 18.0° C., 18.5° C., 19.0° C., 19.5° C., 20.0° C., 20.5° C., 21.0° C., 21.5° C., 22.0° C., 22.5° C., 23.0° C., 23.5° C., 24.0° C., 24.5° C., 25.0° C., and any number or range in between, than the second melting temperature of 5' end common sequences included in first forward and first reverse primers.

In some aspects, second forward and second reverse primers of primer sets provided herein include a tag or a label. A tag or a label can be used for detection of amplicons generated by PCR, for example. Any type of tag or label can be used, including color tags or labels. Exemplary color tags or labels include fluorophores. Any fluorophore can be used, including, for example, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue, Texas Red (available from Invitrogen, for example), and others described in the 11th Edition of the Molecular Probes Handbook by Richard P. Haugland, hereby expressly incorporated by reference in its entirety. Other fluorophores include, for example, Cy3-dCTP, Cy3-dUTP, Cy5-dCTP, Cy5-dUTP (GE Healthcare), fluorescein-12-dUTP, tetramethylrhodamine-6-dUTP, Texas Red®-5- dUTP, Cascade Blue®-7-dUTP, BODIPY® FL-14-dUTP, BODIPY®R-14-dUTP BODIPY® TR-14-dUTP, Rhodamine Green™-5-dUTP, Oregon Green® 488-5-dUTP, Texas Red®-12-dUTP, BODIPY® 630/650-14-dUTP, BODIPY® 650/665-14-dUTP, Alexa Fluor® 488-5-dUTP, Alexa Fluor® 532-5-dUTP, Alexa Fluor® 568-5-dUTP, Alexa Fluor® 594-5-dUTP, Alexa Fluor® 546-14-dUTP, fluorescein-12-UTP, tetramethylrhodamine-6-UTP, Texas Red®-5-UTP, Cascade Blue®-7-UTP, BODIPY® FL-14-UTP, BODIPY® TMR-14-UTP, BODIPY® TR-14-UTP, Rhodamine Green™-5-UTP, Alexa Fluor® 488-5-UTP, and Alexa Fluor® 546-1 4-UTP (Invitrogen), Alexa Fluor® 350, Alexa Fluor® 532, Alexa Fluor® 546, Alexa Fluor® 568, Alexa Fluor® 594, Alexa Fluor® 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, and Cy2, Cy3.5, Cy5.5, and Cy7 (GE Healthcare).

Provided herein, in some embodiments, are methods for determining quality of nucleic acid in a sample.

Methods of determining nucleic acid quality in a sample provided herein can include preparing a polymerase chain reaction (PCR) mixture. The PCR mixture can include a first set of primers including a plurality of first forward primers and a plurality of first reverse primers. Each first forward primer and each first reverse primer can include a 3' end sequence with complementarity to a repetitive sequence present in the nucleic acid and having a first melting temperature. Each first forward and each first reverse primer can also include a 5' end common sequence not present in the nucleic acid and having a second melting temperature. The second melting temperature can be greater than the first melting temperature. In some aspects, first forward and first reverse primers are included in PCR reaction mixtures at low or limiting final concentrations, such as about 0.05 μM, about 0.04 μM, about 0.03 μM, about 0.02 μM, about 0.01 μM, about 0.009 μM, about 0.008 μM, about 0.007 μM, about 0.006 μM, about 0.005 μM, about 0.004 μM, about 0.003 μM, about 0.002 μM, about 0.001 μM, and any number or range in between. In some aspects, the final concentration of first forward and first reverse primers is the same or similar. As used herein, "similar primer concentration" refers to primer concentrations that do not differ by more than 2-fold or less.

The PCR mixture can also include a second set of primers. The second set of primers can include a plurality of second forward primers and a plurality of second reverse primers. Each second forward primer and each second reverse primer can include a 5' end common sequence. In some aspects, second forward and second reverse primers are included in PCR reaction mixtures at a final concentration corresponding to a large molar excess, such as 0.05 μM, 0.06 μM, 0.07 μM, 0.08 μM, 0.09 μM, 0.1 μM, 0.2 μM, 0.3 μM, 0.4 μM, 0.5 μM, 0.6 μM, 0.7 μM, 0.8 μM, 0.9 μM, 1.0 μM, 1.5 μM, 2.0 μM, and any number or range in between. In some aspects, second forward and second reverse primers are included in PCR reaction mixtures at a final concentration of 0.1 μM-0.5 μM. In some aspects, the final concentration of second forward and second reverse primers is the same or similar.

In some aspects, the final concentration of second forward and second reverse primers included in PCR reaction mixtures is greater than the final concentration of first forward and first reverse primers included in PCR reaction mixtures.

The final concentration of second forward and second reverse primers included in PCR reaction mixtures that corresponds to large molar excess can be greater than the final concentration of first forward and first reverse primers that corresponds to a low or limiting concentration. In some aspects, the final concentration of second forward and second reverse primers included in PCR reaction mixtures is at least 2-fold, at least 3-fold, at least 4-fold, at least 5-fold, at least 6-fold, at least 7-fold, at least 8-fold, at least 9-fold, at least 10-fold, at least 15-fold, at least 20-fold, at least 25-fold, at least 30-fold, at least 35-fold, at least 40-fold, at least 45-fold, at least 50-fold, at least 55-fold, at least 60-fold, at least 65-fold, at least 70-fold, at least 75-fold, at least 80-fold, at least 85-fold, at least 90-fold, at least 95-fold, at least 100-fold, at least 200-fold, at least 300-fold, at least 400-fold, at least 500-fold, at least 600-fold, at least 700-fold, at least 800-fold, at least 900-fold, at least 1,000-fold, at least 2,000-fold, at least 3,000-fold, at least 4,000-fold, at least 5,000-fold, at least 6,000-fold, at least 7,000-fold, at least 8,000-fold, at least 9,000-fold, at least 10,000-fold, at least 50,000-fold, at least 100,000-fold, and any number or range in between, greater than the final concentration of first forward and first reverse primers.

Any primer sets included in systems of primers provided herein can be included in a PCR mixture of the methods for determining nucleic acid quality provided herein.

PCR mixtures of the methods for determining nucleic acid quality in a sample provided herein can include a first set of primers. A first set of primers can include a plurality of first forward primers. A first set of primers can also include a plurality of first reverse primers. Each first forward primer and each first reverse primer of a plurality of first forward primers and first reverse primers can include a 3' end sequence with complementarity to a repetitive sequence in the nucleic acid whose quality is determined using the methods provided herein. Each first forward primer and each first reverse primer of a plurality of first forward and first reverse primers can also include a 5' end common sequence not present in the nucleic acid whose quality is determined. Accordingly, primers included in a first set of primers can be hybrid primers, as described above. 3' end sequences with complementarity to repetitive nucleic acid sequences can exhibit perfect or complete complementarity to a repetitive sequence in the nucleic acid. 3' end sequences with complementarity to repetitive nucleic acid sequences can also exhibit substantial complementarity to a repetitive sequence in the nucleic acid.

Each first forward primer and each first reverse primer can include the same 5' common end sequence. The 3' end sequence of each first forward primer and each first reverse primer can vary. 3' end sequences of first forward primers and first reverse primers can be of any length, including about 15, about 16, about 17, about 18, about 19, about 20, about 21, about 22, about 23, about 24, about 25, about 26, about 27, about 28, about 29, about 30, about 31, about 32, about 34, about 35 nucleotides. Any number of different 3' end sequences can be included in first forward primers and first reverse primers of a first set of primers included in PCR mixtures of the methods provided herein. For example, first forward primers and first reverse can include about 1, about 2, about 3, about 4, about 5, about 6, about 7, about 8, about 9, about 10, about 11, about 12, about 13, about 14, about 15, about 16, about 17, about 18, about 19, about 20 different 3' end sequences.

Any combination of different numbers of 3' sequences can be included in first forward primers and first reverse primers of PCR mixtures prepares in the methods provided herein.

For example, first forward primers can have four different 3' end sequences. In some aspects, first forward primers include a sequence of SEQ ID NO:3, SEQ ID NO:4, SEQ ID NO:5, SEQ ID NO:8, or any combination thereof. In some aspects, first reverse primers include three different 3' end sequences. In some aspects, first reverse primers include a sequence of SEQ ID NO:7, SEQ ID NO:10, SEQ ID NO:12, or any combination thereof. Accordingly, first sets of primers of PCR mixtures prepared in the methods provided herein can include an unequal number of first forward primers and first reverse primers. As an example, first forward primers can include four different 3' end sequences and a 5' end common sequence, and first reverse primers can include three different 3' end sequences and a 5' end common sequence. A first set of primers of PCR mixtures prepared in the methods provided herein can also include an equal number of first forward primers and first reverse primers. As an example, first forward primers and first reverse primers can include the same number of different 3' end sequences and a 5' end common sequence. In some aspects, the first set of primers includes about 1 to 20 first forward primers. In some aspects, the first set of primers includes about 1 to 20 first reverse primers. A first set of primers can include any number of first forward primers and any number of first reverse primers.

5' end common sequences can be of any length, including about 15, about 16, about 17, about 18, about 19, about 20, about 21, about 22, about 23, about 24, about 25, about 26, about 27, about 28, about 29, about 30, about 31, about 32, about 34, about 35 nucleotides. 5' end common sequences of first forward and first reverse primers can include the same or substantially the same sequences. 5' end common sequences of first forward primers and first reverse primers can include any sequence that is not present in the nucleic acid analyzed for quality using the methods provided herein. In some aspects, 5' end common sequences of first forward primers include a sequence of SEQ ID NO:1. In some aspects, 5' end common sequences of first reverse primers include a sequence of SEQ ID NO:2.

3' end sequences of first forward and first reverse primers included in PCR mixtures of the methods for determining nucleic acid quality provided herein can have a first melting temperature. 5' end common sequences of first forward and first reverse primers included in PCR mixtures of methods for determining nucleic acid quality can have a second melting temperature. The second melting temperature can be greater than the first melting temperature. In some aspects, the second melting temperature is greater than the first melting temperature by about 5° C. to 25° C. The first melting temperature can be about 45° C. to 70° C. In some aspects, the first melting temperature is about 45° C. to 50° C., about 45° C. to 55° C., about 45° C. to 60 about 45° C., to 65° C., about 45° C. to 70° C. In some aspects, by way of example, the first melting temperature is about 70° C. to 65° C., about 70° C. to 60° C., about 70° C. to 55° C., about 70° C. to 50° C., about 70° C. to 45° C. In some aspects, the first melting temperature is about 50° C. to 53° C. In some aspects, the first melting temperature is about 50.7° C. to 52.5° C. In some aspects, the first melting temperature is about 50.7° C. to 52.5° C. Generally, melting temperatures of 3' end sequences of first forward and first reverse primers are within 0.1° C., 0.5° C., 1.0° C., 1.5° C., 2.0° C., 2.5° C., 3.0° C., 3.5° C., 4.0° C., 4.5° C., 5.0° C., and any number or range in between, of each other.

The second melting temperature can be about 60° C. to 85° C. In some aspects, by way of example, the second melting temperature is about 60° C. to 85° C., about 60° C. to 80° C., about 60° C. to 75° C., about 60° C. to 70° C., about 60° C. to 65° C. In some aspects, the second melting temperature is about 80° C. to 85° C., about 75° C. to 85° C., about 70° C. to 85° C., about 65° C. to 85° C., about 60° C. to 85° C. In some aspects, the second melting temperature is about 70° C. to 75° C. In some aspects, the second melting temperature is about 70° C. to 73° C. In some aspects, the second melting temperature is about 70° C. to 72° C. In some aspects, the second melting temperature is about 70° C. to 71° C. In some aspects, the second melting temperature is about 70° C. to 70.9° C.

First forward primers and first reverse primers of first primer sets included in PCR mixtures can include a 3' end sequence with complementarily to a repetitive sequence in the nucleic acid whose quality is determined using the methods for determining nucleic acid quality in a sample provided herein. The repetitive nucleic acid sequence can include a retrotransposon. A 3' end sequence can have complementarity to any retrotransposon, including LTR and non-LTR retrotransposons. Exemplary retrotransposons include Ty1-copia-like (Pseudoviridae), Ty3-gypsy-like (Metaviridae), and BEL-Pao-like groups of retrotransposons; any group of LINEs, including L1, L2, L3, RTE, R2, I, and Jockey, and Tad, CRE, Deceiver, and Inkcap-like elements; and SINEs, such as CORE-SINEs, V-SINEs, and AmnSINEs.

3' end sequences of first forward primers and first reverse primers of first primer sets of PCR mixtures prepared in the methods provided herein can have complementarity to a sequence of any retrotransposon from any organism. For example, 3' end sequences of first forward and first reverse primers can be designed based on the source of nucleic acid whose quality is determined using the methods provided herein, Thus, 3' end sequences can have complementarity to retrotransposons found in the organism the nucleic acid whose quality is determined is obtained from. The nucleic acid can be from a human. In some aspects, the retrotransposon is a L1 retrotransposon.

3' end sequences of first forward and first reverse primers can be designed to have complementarity to staggered sequences along both strands of a retrotransposon. Staggered sequences along both strands of a retrotransposon can be non-overlapping. In some aspects, each first forward primer can generate amplicons with each first reverse primer, and each first reverse primer can generate amplicons with each first forward primer. In this manner, numerous amplicons can be generated along a range of sizes, including about 50 to 200 bp, about 50 to 300 bp, about 50 to 400 bp, about 50 to 500 bp, about 50 to 600 bp, about 50 to 700 bp, about 50 to 800 bp, about 50 to 900 bp, about 50 to 1,000 bp, about 50 to 1,500 bp, about 50 to 2,000 bp, about 50 to 2,500 bp, about 50 to 3,000 bp, about 50 to 3,500 bp, about 50 to 4,000 bp, about 50 to 4,500 bp, about 50 to 5,000 bp. In some aspects, amplicons range from about 100 to 2,000 bp.

PCR mixtures prepared in methods for determining quality of nucleic acids in a sample provided herein can include a second set of primers. The second set of primers can include a plurality of second forward primers and a plurality of second reverse primers. Each second forward primer and each second reverse primer can include a 5' end common sequence.

A 5' end common sequence included in first forward and first reverse primers can be included in second forward and second reverse primers. In some aspects, second forward and second reverse primers include only a 5' end common sequence included in first forward and first reverse primers and no other sequences or nucleotides. In some aspects, second forward and second reverse primers can include other sequences or nucleotides in addition to a 5' end common sequence included in first forward and first reverse primers. For example, second forward and second reverse primers can include 1, 2, 3, 4, 5, 6, 7, 8, 9, 10, or more additional nucleotides upstream or 5' of the 5' end common sequence. As another example, second forward and second reverse primers can also include 1, 2, 3, 4, 5, 6, 7, 8, 9, 10, or more additional nucleotides downstream or 3' of the 5' end common sequence. Additional sequences or nucleotides downstream or 3' of the 5' end common sequence can include 5' nucleotides present in the 3' end sequence of first forward and first reverse primers without including all of the nucleotides present in the 3' end sequence of first forward and first reverse primers. Thus, additional nucleotides included downstream or 3' of the 5' end common sequence of second forward and second reverse primers can extend into 3' end sequences included in first forward and first reverse primers. In some aspects, 3' end sequences included in second forward and second reverse primers include at least 5, at least 6, at least 7, at least 8, at least 9, at least 10, at least 11, at least 12, at least 13, at least 14, at least 15, at least 16, at least 17, at least 18, at least 19, at least 20 fewer 3' nucleotides than 3' end sequences included in first forward and first reverse primers. Accordingly, in some aspects, 3' end sequences of first forward and first reverse primers include at least 5, at least 6, at least 7, at least 8, at least 9, at least 10, at least 11, at least 12, at least 13, at least 14, at least 15, at least 16, at least 17, at least 18, at least 19, at least 20 more 3' nucleotides than 3' end sequences included in second forward and second reverse primers.

Any combination of second forward and second reverse primers can be included in the second set of primers of PCR mixtures prepared in the methods for determining nucleic acid quality provided herein, including second forward primers that include a 5' end common sequence, second forward primers that include a 5' end common sequence and any number of additional nucleotides, second reverse primers that include a 5' end common sequence, and second reverse primers that include a 5' end common sequence and any number of additional nucleotides. Accordingly, a second set of primers can include an equal number of second forward and second reverse primers. A second set of primers can also include an unequal number of second forward and second reverse primers. In some aspects, the second set of primers includes about 1 to 20 second forward primers. In some aspects, the second set of primers includes about 1 to 20 second reverse primers. A second set of primers can include any number of second forward primers and any number of second reverse primers.

Second forward and second reverse primers can have a melting temperature that is greater than the first melting temperature of 3' end sequences of first forward and first reverse primers. The melting temperature of second forward and second reverse primers can be similar to or correspond to the second melting temperature of 5' end common sequences of first forward and first reverse primers. For example, where second forward and second reverse primers do not include sequences other that 5' end common sequences, the melting temperature of second forward and second reverse primers can correspond to the second melting temperature of 5' end common sequences included in first forward and first reverse primers. As another example, where second forward and second reverse primers include nucleotides in addition to 5' end common sequences, the melting temperature of second forward and second reverse primers can be greater than the second melting temperature of 5' end common sequences included in first forward, and first reverse primers. The melting temperature of second forward and second reverse primers can be greater by about 0.5° C., 1.0° C., 1.5° C., 2.0° C., 2.5° C., 3.0° C., 3.5° C., 4.0° C., 4.5° C., 5.0° C., 5.5° C., 6.0° C., 6.5° C., 7.0° C., 7.5° C., 8.0° C., 8.5° C., 9.0° C., 9.5° C., 10.0° C., 10.5° C., 11.0° C., 11.5° C., 12.0° C., 12.5° C., 13.0° C., 13.5° C., 14.0° C., 14.5° C., 15.0° C., 15.5° C., 16.0° C., 16.5° C., 17.0° C., 17.5° C., 18.0° C., 18.5° C., 19.0° C., 19.5° C., 20.0° C., 20.5° C., 21.0° C., 21.5° C., 22.0° C., 22.5° C., 23.0° C., 23.5° C., 24.0° C., 24.5° C., 25.0° C., and any number or range in between, than the second melting temperature of 5' end common sequences included in first forward and first reverse primers.

In some aspects, second forward and second reverse primers of primer sets used in the methods provided herein include a tag or a label. A tag or a label can be used for detection of amplicons generated by PCR, for example. Any type of tag or label can be used, including color tags or labels. Exemplary color tags or labels include a fluorophore. Any fluorophore can be used, including, for example, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue, Texas Red (available from Invitrogen, for example), and others described in the 11th Edition of the Molecular Probes Handbook by Richard P. Haugland, hereby expressly incorporated by reference in its entirety. Other fluorophores include, for example, Cy3-dCTP, Cy3-dUTP, Cy5-dCTP, Cy5-dUTP (GE Healthcare), fluorescein-12-dUTP, tetramethylrhodamine-6-dUTP, Texas Red®-5-dUTP, Cascade Blue®-7-dUTP, BODIPY® FL-14-dUTP, BODIPY®R-14-dUTP, BODIPY® TR-14-dUTP, Rhodamine Green™-5-dUTP, Oregon Green® 488-5-dUTP, Texas Red®-12-dUTP, BODIPY® 630/650-14-dUTP, BODIPY® 650/665-14-dUTP, Alexa Fluor® 488-5-dUTP, Alexa Fluor® 532-5-dUTP, Alexa Fluor® 568-5-dUTP, Alexa Fluor® 594-5-dUTP, Alexa Fluor® 546-1 4-dUTP, fluorescein-12-UTP, tetramethylrhodamine-6-UTP, Texas Red®-5-UTP, Cascade Blue®-7-UTP, BODIPY® FL-14-UTP, BODIPY® TMR-14-UTP, BODIPY® TR-14-UTP, Rhodamine Green™-5-UTP, Alexa Fluor® 488-5-UTP, and Alexa Fluor® 546-1 4-UTP (Invitrogen), Alexa Fluor® 350, Alexa Fluor® 532, Alexa Fluor® 546, Alexa Fluor® 568, Alexa Fluor® 594, Alexa Fluor® 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, and Cy2, Cy3.5, Cy5.5, and Cy7 (GE Healthcare).

Methods of determining the quality of nucleic acid in a sample provided herein can include performing a first polymerase chain reaction (PCR) on the sample. In some aspects, the first elongation step of each cycle in the first PCR is at a temperature of about the first melting temperature of 3' end sequences of first forward and first reverse primers included in PCR reaction mixtures provided herein. In some aspects, the first elongation step is at a temperature that is about 5° C. below the first melting temperature to 5° C. above the first melting temperature. In some aspects, the first elongation step is at a temperature that is at least 5° C. below the second melting temperature. In some aspects, the first elongation step is at a temperature that is about 5° C. below the first melting temperature to 5° C. above the first melting temperature and at least 5° C. below the second melting temperature. In some aspects, the first elongation step is at about 45° C. to 70° C. In some aspects, the first elongation step is at about 45° C. to 50° C., about 45° C. to 55° C., about 45° C. to 60° C., about 45° C. to 65° C., about 45° C. to 70° C. In some aspects, by way of example, the first elongation step is at about 70° C. to 65° C., about 70° C. to 60° C., about 70° C. to 55° C., about 70° C. to 50° C., about 70° C. to 45° C. In some aspects, the first elongation step is at about 50° C. to 53° C. In some aspects, the first elongation step is at about 50.7° C. to 52.5° C. In some aspects, the first elongation step is at about 50° C.

The first elongation step can be of any suitable length of time. For example, the first elongation step can be for about 30 seconds, about 40 seconds, about 50 seconds, about 1 minute, about 1 minute 10 seconds, about 1 minute 20 seconds, about 1 minute 30 seconds, about 1 minute 40 seconds, about 1 minute 50 seconds, about 2 minutes, about 2 minutes 10 seconds, about 2 minutes 20 seconds, about 2 minutes 30 seconds, about 2 minutes 40 seconds, about 2 minutes 50 seconds, about 3 minutes, and any number or range in between. In some aspects, the first elongation step is for about 2 minutes.

The first PCR can include any suitable number of cycles. Generally, the cycle number of the first PCR is below 10 cycles, although a greater number of cycles can also be performed. The first PCR can be for about 1 cycle, about 2 cycles, about 3 cycles, about 4 cycles, about 5 cycles, about 6 cycles, about 7 cycles, about 8 cycles, about 9 cycles, about 10 cycles. In some aspects, the first PCR includes about 3-5 cycles.

Methods of determining the quality of nucleic acid in a sample provided herein can include performing a second polymerase chain reaction (PCR) on the sample. In some aspects, the second elongation step of each cycle in the second PCR is at a temperature of about the second melting temperature of 5' end common sequences of second forward and second reverse primers included in PCR reaction mixtures provided herein. In some aspects, the second elongation step is at a temperature that is about 5° C. below the second melting temperature to 5° C. above the second melting temperature. In some aspects, the second elongation step is at a temperature that is at least 5° C. above the first melting temperature. In some aspects, the second elongation step is at a temperature that is about 5° C. below the second melting temperature to 5° C. above the second melting temperature and at least 5° C. above the first melting temperature. In some aspects, the second elongation step is at about 60° C. to 85° C. In some aspects, by way of example, the second elongation step is at about 60° C. to 85° C., about 60° C. to 80° C., about 60° C. to 75° C., about 60° C. to 70° C., about 60° C. to 65° C. In some aspects, the second elongation step is at about 80° C. to 85° C., about 75° C. to 85° C., about 70° C. to 85° C., about 65° C. to 85° C., about 60° C. to 85° C. In some aspects, the second elongation step is at about 70° C. to 75° C. In some aspects, the second elongation step is at about 70° C. to 73° C. In some aspects, the second elongation step is at about 70° C. to 72° C. In some aspects, the second elongation step is at about 70° C. to 71° C. In some aspects, the second elongation step is at about 70° C. to 70.9° C. In some aspects, the second elongation step is at about 70° C.

The second elongation step can be of any suitable length of time. For example, the second elongation step can be for about 30 seconds, about 40 seconds, about 50 seconds, about 1 minute, about 1 minute 10 seconds, about 1 minute 20 seconds, about 1 minute 30 seconds, about 1 minute 40 seconds, about 1 minute 50 seconds, about 2 minutes, about 2 minutes 10 seconds, about 2 minutes 20 seconds, about 2 minutes 30 seconds, about 2 minutes 40 seconds, about 2 minutes 50 seconds, about 3 minutes, and any number or range in between. In some aspects, the second elongation step is for about 1 minute.

The second PCR can include any suitable number of cycles. Generally, the cycle number of second PCR is greater than 10 cycles, although fewer numbers of cycles can also be performed. The second PCR can be for about 10 cycles, 11 cycles, about 12 cycles, about 13 cycles, about 14 cycles, about 15 cycles, about 16 cycles, about 17 cycles, about 18 cycles, about 19 cycles, about 20 cycles, about 21 cycles, about 22 cycles, about 23 cycles, about 24 cycles, about 25 cycles, about 26 cycles, about 27 cycles, about 28 cycles, about 29 cycles, about 30 cycles, about 31 cycles, about 32 cycles, about 34 cycles, about 35 cycles, about 36 cycles, about 37 cycles, about 38 cycles, about 39 cycles, about 40 cycles, about 41 cycles, about 42 cycles, about 43 cycles, about 44 cycles, about 45 cycles, about 46 cycles, about 47 cycles, about 48 cycles, about 49 cycles, about 50 cycles, or more cycles. In some aspects, the second PCR includes about 10-35 cycles. In some aspects, the second PCR includes about 15-25 cycles.

Methods for determining quality of nucleic acid in a sample provided herein can include determining a size range of amplicons. As used herein, "amplicon" means a nucleic acid that is the product of amplification or replication events, such as polymerase chain reaction (PCR), ligase chain reaction (LCR), or gene duplication, for example. Where referring to a product of an amplification reaction such as PCR, the terms "amplicon" and "PCR product" can be used interchangeably, unless context clearly indicates otherwise.

First forward and first reverse primers can be designed to have complementarity at their 3' end to staggered and/or non-overlapping sequences along both strands of a retrotransposon. Because each first forward primer can generally generate amplicons with each first reverse primer, and each first reverse primer can generally generate amplicons with each first forward reverse primer, numerous amplicons can be generated alone a range of sizes using the methods provided herein, including about 50 to 200 bp, about 50 to 300 bp, about 50 to 400 bp, about 50 to 500 bp, about 50 to 600 bp, about 50 to 700 bp, about 50 to 800 bp, about 50 to 900 bp, about 50 to 1,000 bp, about 50 to 1,500 bp, about 50 to 2,000 bp, about 50 to 2,500 bp, about 50 to 3,000 bp, about 50 to 3,500 bp, about 50 to 4,000 bp, about 50 to 4,500 bp, about 50 to 5,000 bp. In some aspects, amplicons range from about 100 to 2,000 bp. The size range of any amplicons generated by the methods provided herein can be used for analysis of nucleic acid quality.

Methods of determining nucleic acid quality provided herein can include determining intensity ratios of amplicons. Any suitable methodology can be used to determine amplicon size and amplicon intensity ratios, including the Agilent 4200 TapeStation system, the Agilent 2200 TapeStation system, the Agilent 2100 Bioanalyzer system, Agilent DNA ScreenTape Analysis, Agilent D1000 and High Sensitivity D1000 Screen Tape Assays, Lab901 TapeStation, and Shimadzu MCE-202 MultiNA, and others. In some aspects, a presence of predicted amplicon sizes correlates with nucleic acid quality. In some aspects, a presence of predicted amplicon sizes correlates with nucleic acid size. In some aspects, a presence of predicted amplicon intensities correlates with nucleic acid quality. In some aspects, a presence of predicted amplicon intensities correlates with nucleic acid quality.

As used herein, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as is commonly understood by one of skill in the art to which this invention belongs.

"About" as used herein when referring to a measurable value such as an amount, a temporal duration, and the like, is meant to encompass variations of ±20% or ±10%, or ±5%, or even ±1% from the specified value, as such variations are appropriate for the disclosed compositions or to perform the disclosed methods.

As used herein, the term "nucleic acid" refers to any deoxyribonucleic acid (DNA) molecule, ribonucleic acid (RNA) molecule, or nucleic acid analogues. A DNA or RNA molecule can be double-stranded or single-stranded and can be of any size. Exemplary nucleic acids include, but are not limited to, chromosomal DNA, plasmid DNA, cDNA, cell-free DNA (cfDNA), circulating tumor DNA (ctDNA), mRNA, tRNA, rRNA, siRNA, micro RNA (miRNA or miR), hnRNA. Exemplary nucleic analogues include peptide nucleic acid, morpholino- and locked nucleic acid, glycol nucleic acid, and threose nucleic acid. As used herein, the terms "nucleic acid molecule" and "nucleic acid" are meant to include fragments of nucleic acid molecules and nucleic acids as well as any full-length or non-fragmented nucleic acid molecule and nucleic acid, for example.

As used herein, the term "nucleotide" includes both individual units of ribonucleic acid and deoxyribonucleic acid as well as nucleoside and nucleotide analogs, and modified nucleotides such as labeled nucleotides. In addition, "nucleotide" includes non-naturally occurring analogue structures, such as those in which the sugar, phosphate, and/or base units are absent or replaced by other chemical structures. Thus, the term "nucleotide" encompasses individual peptide nucleic acid (PNA) (Nielsen et al., Bioconjug. Chem. 1994; 5(1):3-7) and locked nucleic acid (LNA) (Braasch and Corey, Chem. Biol. 2001; 8(1): 1-7) units as well as other like units.

As used herein, the terms "sample" and "biological sample" refer to any sample suitable for use with the compositions and methods provided herein. A sample used with the present compositions and methods can be obtained from tissue samples or bodily fluid from a subject, or tissue obtained by a biopsy procedure (e.g., a needle biopsy) or a surgical procedure. The biological sample of the present methods can be a sample of bodily fluid, e.g., cerebrospinal fluid (CSF), blood, serum, plasma, urine, saliva, tears, and ascites, for example. A sample of bodily fluid can be collected by any suitable method known to a person of skill in the art.

As used herein, the term "subject" refers to any individual or patient on which the methods disclosed herein are performed. The term "subject" can also include any individual or patient that is a source of nucleic acids for use with the compositions and the methods provided herein. The term "subject" can be used interchangeably with the term "individual" or "patient." The subject can be a human, although the subject may be an animal, as will be appreciated by those in the art. Thus, other animals, including mammals such as rodents (including mice, rats, hamsters and guinea pigs), cats, dogs, rabbits, farm animals including cows, horses, goats, sheep, pigs, etc., primates (including monkeys, chimpanzees, orangutans and gorillas), reptiles, birds, amphibians, bony fish, cartilageous fish, and invertebrates are included within the definition of subject. The subject may also be a plant or microorganism.

Example 1

This example describes design of a novel assay that provides a broader range of DNA sizes for analysis of nucleic acid quality from a single amplification reaction, can be used with lower amounts of DNA, and is less susceptible to DNA variation at individual sites.

Current methods for determination of DNA quality are insufficient for effectively assessing whether a sample should proceed to library preparation for next generation sequencing (NGS), for example. Having a functional assay that predicts success at whether a sample can be successfully converted would be very useful. The Quantitative Functional Index (QFI) assay examines a few DNA segments for amplifiability but the limited number of fragments and sizes limits its usefulness. Therefore, an assay was generated that amplifies many more genomic fragments over a more relevant size range to improve assay predictability.

The novel assay for determining DNA quality relies on the amplification of repetitive sequences in the human genome, with a small number of primers able to amplify hundreds or more distinct sites on the genome. These primers can amplify regions relevant to NGS so that a more accurate view of DNA quality can be generated.

Primers were designed based on the sequence of the highly repeated 5' end of the L1 retrotransposon. Staggered sequences along both strands were selected so as to have uniform melting temperatures and generate fragment sizes in the range of 107-833 bp. Each of the seven primers selected should generate >68 different amplicons with each of the other primers on the opposite strand. This leads to fragments with many sizes in the 100-2,000 bp region. FIG. 1 provides an overview of DNA primers and assay methods.

The L1 binding primers are fused to a common sequence not present in human DNA with one sequence added to the + strand primers and a second sequence fused to the – strand primers. Bases adjacent to the fusion point were chosen to minimize overlap with the L1 sequences. The fused primers are then added to the amplification mix at low concentration and used to amplify genomic DNA at the Tm of the L1 sequences for only a small number of cycles (e.g., 3-5 cycles, with cycle number able to be optimized). FIG. 2 shows representative LINE sequences for initial PCR together with expected amplicon lengths and the number of predicted amplicons.

After the small number of cycles, the temperature is raised to the Tm of the 5' end fusion sequences and the large molar excess of the fusion primers then amplifies the reaction for many more cycles (e.g., 15-25 cycles, with cycle number able to be optimized). This generates a large range of DNA fragments that is separated on standard DNA sizing instruments (such as a TapeStation, DNA sequencer, or other method for separating DNA by size). The intensity ratios at specific sizes or size ranges are used to correlate with DNA size and quality. Primers and primer components are shown in FIG. 3. A size distribution of predicted amplicons is shown in FIG. 4.

A number of modifications of the assay are possible. For example, the common primers can be extended by one or a few bases into the L1 sequence and labeled with different color tags so that better resolution of specific fragments could occur. Different primers can also be used for possible improved performance, for example.

The benefits of this method derive from the use of repetitive DNA as the starting material. The presence of 100s to 1000s times more copies of the DNA per genome allows for detection of much smaller amounts of DNA and the use of very small amounts of starting material. Because many of the DNA fragments have slightly different sizes, more sizes are interrogated compared to a standard QFI assay. In addition, because regions from throughout the genome are examined, changes to a single region of the genome will not have a substantial effect on the assay.

In summary, a novel assay for the determination of nucleic acid quality was designed based on the analysis of repetitive nucleic acid sequences. The novel assay is useful for determining nucleic acid quality for applications such as library preparation and next generation sequencing (NGS), for example, and any other applications for which nucleic acid quality is important.

SEQUENCES

SEQ ID NO: 1
TTCGGAACTCCTACGAGGTCCACT

SEQ ID NO: 2
TCGCATCAGAGTCATCGTTGACC

SEQ ID NO: 3
GAGATATGTGACCTTTCAG

SEQ ID NO: 4
AGGAAACTCAAAGAAATT

SEQ ID NO: 5
AGAATCAAGCAGAAATTC

SEQ ID NO: 6
CAGAAGAAAGAATTAGTGAG

SEQ ID NO: 7
CTCACTAATTCTTTCTTCTG

SEQ ID NO: 8
TAGAAAATAGCCTCAAAAG

-continued

SEQUENCES

SEQ ID NO: 9
CCCAAACCTAGAGAAAG

SEQ ID NO: 10
CTTTCTCTAGGTTTGGG

SEQ ID NO: 11
AGAAATGCTAAAGGGAG

SEQ ID NO: 12
CTCCCTTTAGCATTTCT

| SEQ ID NO. | Description |
|---|---|
| SEQ ID NO.: 1 | 5' end common sequence; forward primer |
| SEQ ID NO.: 2 | 5' end common sequence; reverse primer |
| SEQ ID NO.: 3 | DF0000227 position 909; L1 (LINE) sequence for initial PCR and forward primer |
| SEQ ID NO.: 4 | DF0000227 position 954; L1 (LINE) sequence for initial PCR and forward primer |
| SEQ ID NO.: 5 | DF0000227 position 1042; L1 (LINE) sequence for initial PCR and forward primer |
| SEQ ID NO.: 6 | DF0000227 position 1148; L1 (LINE) sequence for initial PCR |
| SEQ ID NO.: 7 | DF0000227 position 1148; reverse primer |
| SEQ ID NO.: 8 | DF0000227 position 1234; L1 (LINE) sequence for initial PCR and forward primer |
| SEQ ID NO.: 9 | DF0000227 position 1358; L1 (LINE) sequence for initial PCR |
| SEQ ID NO.: 10 | DF0000227 position 1358; reverse primer |
| SEQ ID NO.: 11 | DF0000227 position 1742; L1 (LINE) sequence for initial PCR |
| SEQ ID NO.: 12 | DF0000227 position 1742; reverse primer |

Any and all references and citations to other documents, such as patents, patent applications, patent publications, journals, books, papers, web contents, that have been made throughout this disclosure are hereby incorporated herein by reference in their entirety for all purposes.

Although the invention has been described with reference to the above example, it will be understood that modifications and variations are encompassed within the spirit and scope of the invention. Accordingly, the invention is limited only by the following claims.

What is claimed is:

1. A system for determining the quality of nucleic acid in a sample comprising:

(a) a first set of primers comprising a plurality of first forward primers and a plurality of first reverse primers, each first forward primer and each first reverse primer comprising:

(i) a 3' end sequence with complementarity to a repetitive sequence in the nucleic acid and having a first melting temperature; and (ii) a 5' end common sequence not present in the nucleic acid and having a second melting temperature, wherein the second melting temperature is greater than the first melting temperature, and wherein the 5' end common sequence of each first forward primer comprises a sequence of SEQ ID NO: 1 and the 5' end common sequence of each first reverse primer comprises a sequence of SEQ ID NO:2; and (b) a second set of primers comprising a plurality of second forward primers and a plurality of second reverse primers, each second forward primer and each second reverse primer comprising a 5' end common sequence.

2. The system of primers of claim 1, wherein the second melting temperature is greater than the first melting temperature by about 5° C. to 25° C.

3. The system of primers of claim 1, wherein the first melting temperature is about 45° C. to 70° C.

4. The system of primers of claim 1, wherein the second melting temperature is about 60° C. to 85° C.

5. The system of primers of claim 1, wherein the first set of primers comprises an equal number of first forward primers and first reverse primers.

6. The system of primers of claim 1, wherein the first set of primers comprises an unequal number of first forward primers and first reverse primers.

7. The system of primers of claim 1, wherein the second set of primers comprises an equal number of second forward primers and second reverse primers.

8. The system of primers of claim 1, wherein the second set of primers comprises an unequal number of second forward primers and second reverse primers.

9. The system of primers of claim 1, wherein the first set of primers comprises about 1 to 20 first forward primers and about 1 to 20 first reverse primers.

10. The system of primers of claim 1, wherein the second set of primers comprises about 1 to 20 second forward primers and about 1 to 20 second reverse primers.

11. The system of primers of claim 1, wherein the repetitive nucleic acid sequence comprises a retrotransposon.

12. The system of primers of claim 11, wherein the retrotransposon is a L1 retrotransposon.

13. The system of primers of claim 1, wherein the 3' end sequence of each first forward primer comprises a sequence of SEQ ID NO:3, SEQ ID NO:4, SEQ ID NO:5, SEQ ID NO:8, or any combination thereof.

14. The system of primers of claim 1, wherein the 3' end sequence of each first reverse primer comprises a sequence of SEQ ID NO:7, SEQ ID NO:10, SEQ ID NO:12, or any combination thereof.

15. A method for determining quality of nucleic acid in a sample comprising:

(a) preparing a polymerase chain reaction (PCR) mixture comprising:

(i) a first set of primers comprising a plurality of first forward primers and a plurality of first reverse primers, each first forward primer and each first reverse primer comprising:

(i) a 3' end sequence with complementarity to a repetitive sequence in the nucleic acid and having a first melting temperature; and (ii) a 5' end common sequence not present in the nucleic acid and having a second melting temperature, wherein the second melting temperature is greater than the first melting temperature, and wherein the 5' end common sequence of each first forward primer comprises a sequence of SEQ ID NO: 1 and the 5' end common sequence of each first reverse primer comprises a sequence of SEQ ID NO:2; and ii) a second set of primers comprising a plurality of second forward primers and a plurality of second reverse primers, each second forward primer and each second reverse primer comprising a 5' end common sequence;

(b) performing a first polymerase chain reaction (PCR) on the sample, wherein a first elongation step of each cycle in the first PCR is at a temperature of about the first melting temperature;

(c) performing a second polymerase chain reaction (PCR) on the sample to generate a plurality of amplicons, wherein a second elongation step of each cycle in the second PCR is at a temperature of about the second melting temperature; and (d) determining a size or size range of the amplicons.

16. The method of claim 15, wherein the second melting temperature is greater than the first melting temperature by about 5° C. to 25° C.

17. The method of claim 15, wherein the first melting temperature is about 45° C. to 70° C.

18. The method of claim 15, wherein the second melting temperature is about 60° C. to 85° C.

19. The method of claim 15, wherein the first elongation step is at a temperature that is about 5° C. below the first melting temperature to 5° C. above the first melting temperature and that is at least 5° C. below the second melting temperature.

20. The method of claim 15, wherein the second elongation step is at a temperature that is about 5° C. below the second melting temperature to 5.0° C. above the second melting temperature and that is at least 5° C. above the first melting temperature.

21. The method of claim 15, wherein the first elongation step is for about 2 minutes.

22. The method of claim 15, wherein the second elongation step is for about 1 minute.

23. The method of claim 15, wherein the first set of primers comprises an equal number of first forward primers and first reverse primers.

24. The method of claim 15, wherein the first set of primers comprises an unequal number of first forward primers and first reverse primers.

25. The method of claim 15, wherein the second set of primers comprises an equal number of second forward primers and second reverse primers.

26. The method of claim 15 wherein the second set of primers comprises an unequal number of second forward primers and second reverse primers.

27. The method of claim 15, wherein the first set of primers comprises about 1 to 20 first forward primers and about 1 to 20 first reverse primers.

28. The method of claim 15, wherein the second set of primers comprises about 1 to 20 second forward primers and about 1 to 20 second reverse primers.

29. The method of claim 15, wherein a final concentration of second forward primers and second reverse primers is greater than the final concentration of first forward primers and first reverse primers.

30. The method of claim 29, wherein the final concentration of first forward primers is the same or similar to the final concentration of first reverse primers.

31. The method of claim 29, wherein the final concentration of second forward primers is the same or similar to the final concentration of second reverse primers.

32. The method of claim 15, wherein the repetitive nucleic acid sequence comprises a retrotransposon.

33. The method of claim 32, wherein the retrotransposon is a L1 retrotransposon.

34. The method of claim 15, wherein the first PCR comprises about 3 to 5 cycles.

35. The method of claim 15, wherein the second PCR comprises about 10 to 35 cycles.

36. The method of claim 15, wherein the method further comprises predicting intensity ratios for amplicons having an expected size or size range and measuring an intensity ratio of at least one of the amplicons.

37. The method of claim 15, further comprising predicting amplicon sizes and correlating a presence of one or more amplicons of an expected size with nucleic acid quality.

38. The method of claim 15, further comprising predicting amplicon sizes and comparing predicted amplicon sizes with the size of at least one of the amplicons.

39. The method of claim 36, wherein a presence of predicted amplicon intensity ratios correlates with nucleic acid quality.

40. The method of claim 36, wherein a presence of predicted amplicon intensity ratios correlates with nucleic acid size.

41. The method of claim 15, wherein the 3' end sequence of each first forward primer comprises a sequence of SEQ ID NO:3, SEQ ID NO:4, SEQ ID NO:5, SEQ ID NO: 8, or any combination thereof.

42. The method of claim 15, wherein the 3' end sequence of each first reverse primer comprises a sequence of SEQ ID NO:7, SEQ ID NO:10, SEQ ID NO:12, or any combination thereof.

\* \* \* \* \*

SEQUENCE LISTING

<160> NUMBER OF SEQ ID NOS: 12

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ttcggaactc ctacgaggtc cact                                              24

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic -continued

```
          oligonucleotide

<400> SEQUENCE: 2
tcgcatcaga gtcatcgttg acc                                        23

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gagatatgtg acctttcag                                             19

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aggaaactca aagaaatt                                              18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
agaatcaagc agaaattc                                              18

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cagaagaaag aattagtgag                                            20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ctcactaatt ctttcttctg                                            20

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 8
tagaaaatag cctcaaaag                                              19

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cccaaaccta gagaaag                                               17

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ctttctctag gtttggg                                               17

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
agaaatgcta aagggag                                               17

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ctccctttag catttct                                               17
```